(12) United States Patent
Xu et al.

(10) Patent No.: US 12,275,713 B1
(45) Date of Patent: Apr. 15, 2025

(54) METHOD FOR PREPARING 5-HYDROXYMETHYLFURFURAL

(71) Applicant: HEFEI LEAF BIOTECH CO., LTD., Hefei (CN)

(72) Inventors: Hai Xu, Hefei (CN); Qiang Xu, Heifei (CN); Sanxi Yu, Hefei (CN); Xinglong Li, Hefei (CN)

(73) Assignee: HEFEI LEAF BIOTECH CO., LTD., Anhui (CN)

( * ) Notice: Subject to any disclaimer, the term of this patent is extended or adjusted under 35 U.S.C. 154(b) by 0 days.

(21) Appl. No.: 18/895,254

(22) Filed: Sep. 24, 2024

(30) Foreign Application Priority Data

Oct. 30, 2023 (CN) .......................... 202311420375.9

(51) Int. Cl.
*C07D 307/50* (2006.01)
*B01J 23/14* (2006.01)
*B01J 37/02* (2006.01)

(52) U.S. Cl.
CPC ............ *C07D 307/50* (2013.01); *B01J 23/14* (2013.01); *B01J 37/0203* (2013.01)

(58) Field of Classification Search
CPC ...... C07D 307/50; B01J 23/14; B01J 37/0203
USPC ........................................................ 549/488
See application file for complete search history.

(56) References Cited

FOREIGN PATENT DOCUMENTS

| CN | 108404912 A | 8/2018 |
|---|---|---|
| CN | 112625012 | * 4/2021 |

OTHER PUBLICATIONS

Modified molecular sieves for catalytic dehydration of fructose to 5-hydroxymethylfurfural, Jan. 2020,Liu Zhonghai , Gao Sainan , Qin Dongling , Yang Gang.

* cited by examiner

*Primary Examiner* — Taylor V Oh
(74) *Attorney, Agent, or Firm* — Valet Patent Service Limited

(57) ABSTRACT

The application discloses a method for preparing 5-hydroxymethylfurfural and belongs to the technical field of synthesis of 5-hydroxymethylfurfural, mainly using biomass sugar as raw material and catalyzing the sugar to prepare 5-hydroxymethylfurfural in a tubular reactor filled with catalyst particles. In the application, the preparation of the humin-supported Sn catalyst is simple and has mild reaction conditions; the catalyst, as a high value-added product of humin, has good catalytic efficiency; the preparation of 5-hydroxymethylfurfural using the catalyst has the advantages of high yield, low cost and the like; the tubular reactor adopted can reduce backmixing, greatly shorten the reaction time and reduce the generation of humin and can also be equipped with inline monitoring equipment to monitor the preparation of HMF in a timely manner. Therefore, the application has the advantages of simple process, low energy consumption, high yield, cost saving, and the like.

8 Claims, 3 Drawing Sheets

METHOD FOR PREPARING 5-HYDROXYMETHYLFURFURAL

TECHNICAL FIELD

The present application belongs to the technical field of synthesis of 5-hydroxymethylfurfural, and particularly relates to a method for preparing 5-hydroxymethylfurfural.

BACKGROUND

5-Hydroxymethylfurfural (5-HMF) is a platform compound with the advantages of high added value and wide applicability. It can be used as a monomer to synthesize bio-based materials, biofuels, pharmaceutical intermediates, liquid fuels and various chemical products, etc. It has broad application prospects in green, low-carbon and sustainable development. The value-added products derived from 5-HMF typically include 2,5-furandicarboxylic acid (FDCA), 2,5-furandicarboxaldehyde, 2,5-furandimethanol, 5-hydroxymethyl-2-furancarboxylic acid, levulinic acid, 2,5-dimethylfuran, etc. At present, raw materials for preparing 5-HMF are typically cellulose, fructose, sucrose, glucose, etc.

In order to achieve efficient conversion from biomass sugar to 5-HMF, the design and development of catalysts are crucial. A large number of scholars are committed to developing high-performance catalysts. Early research focused on homogeneous catalysts, including organic acids (such as oxalic acid, formic acid, and citric acid), inorganic acids (such as hydrochloric acid, and sulfuric acid), metal salts (metal chlorides), etc. Although organic acids and inorganic acids among the homogeneous catalysts have high catalytic efficiency, they have problems such as corrosion of equipment and environmental pollution. Later, researchers gradually developed heterogeneous catalysts, including strong acidic cation exchange resins, molecular sieves, heteropoly acids, etc. Compared with homogeneous catalysts, heterogeneous catalysts have problems such as high cost, low catalytic efficiency, and complex preparation process. The choice of solvent also has a great influence on the synthesis of 5-HMF, which is typically divided into water, organic solvents, water-organic mixed solvents and ionic liquids. Although water is a green and ideal solvent for the preparation of 5-HMF from biomass sugars (such as glucose, fructose, and cellulose), it has the problem of low selectivity for 5-HMF, and it is easy to generate by-products such as humin, levulinic acid, and formic acid under acid catalysis. One of the main reasons for the low utilization rate of sugar resources is the generation of humin, which is a low-carbon polymer that is insoluble in water and has the characteristics of high molecular weight, high stability, and difficult conversion.

Patent Publication No. CN107556271A proposes a method for preparing 5-HMF from glucose, comprising using glucose and choline chloride as raw materials to form a low eutectic solvent, and the yield of 5-HMF prepared by catalysis under the action of a solid acid catalyst reaches up to 36.23%. The patent uses a low eutectic solvent instead of an aqueous phase to avoid the disadvantage that 5-HMF is unstable in an acidic solution, and the solid acid catalyst is easy to prepare. However, the yield of 5-HMF prepared based on this method is still very low. Patent Publication No. CN106669655A proposes a method for preparing 5-HMF from a carbohydrate compound by catalyzing with a niobium-carbon solid acid catalyst. Catalysts of different strengths were synthesized by adjusting the types of carbon source and niobium precursor and the ratio of the two. Although the catalyst characterization showed that this type of solid acid catalyst exhibited excellent cyclic stability, the yield of 5-HMF prepared using this catalyst could only reach 56% at most. Patent Publication No. CN112625012A proposed a method for preparing 5-HMF from glucose using a tin-modified molecular sieve catalyst. Although the catalyst has high stability, low price, simple preparation process and can achieve one-step catalytic conversion from glucose to 5-HMF, the yield of 5-HMF is still low, and can only reach 58.0% at most.

With the increasing prominence of energy crisis and environmental pollution problems, turning industrial waste into treasure has become the research focus of scholars. For example, the furfural residue produced in the process of biomass hydrolysis contains a large amount of cellulose. Making full use of the added value of furfural residue is of great significance to the industry producing furfural. Humin, as an industrial waste, is generally used for direct combustion and heating, but as a potential carbon material, it can be prepared into high value-added chemicals or materials. Therefore, the rational use of low value-added humin is of great significance to improving the carbon utilization rate in the process of sugar hydrolysis. The present application designs and synthesizes a tin on humin catalyst and applies it to catalyze biomass sugars (such as fructose syrup, glucose syrup, high fructose corn syrup, waste molasses, and straw syrup) to prepare 5-HMF.

SUMMARY

The object of the present application is to provide a method for preparing 5-hydroxymethylfurfural to solve the problems of low raw material utilization and low product purity in the preparation of 5-HMF.

The object of the present application can be achieved through the following technical solution:

A method for preparing 5-hydroxymethylfurfural comprises the following steps:

Step S1, drying and then grinding humin into a first powder, suspending the first powder in water to obtain a suspension, adding a tin tetrachloride aqueous solution under rapid stirring to the suspension, stirring continuously after the addition, standing overnight for aging, performing concentrating and drying, grinding the resultant into a second powder, and calcining the second powder in air to obtain a humin-supported Sn catalyst; and Step S2, injecting a sugar-containing raw material and an organic solvent using a metering pump into a reaction device filled with the humin on tin catalyst for reaction respectively, and after the reaction, performing separation and purification to obtain 5-hydroxymethylfurfural.

As a further embodiment of the present application: the sugar-containing raw material is at least one of fructose syrup, glucose syrup, high fructose corn syrup, waste molasses and straw syrup.

As a further embodiment of the present application: the concentration of the fructose syrup, glucose syrup and high fructose corn syrup is 1%-75%, and the concentration of the waste molasses and straw syrup is 1%-50%.

As a further embodiment of the present application: the organic solvent is at least one of ethyl acetate, acetonitrile, tetrahydrofuran, acetone, toluene, methyl isobutyl ketone, dimethyl sulfoxide, N,N-dimethylformamide, N,N-dimethylacetamide, N-methylpyrrolidone, 2-methyltetrahydrofuran, dimethyl carbonate, 1,4-dioxane, methanol, isopropanol, n-butanol, methyl tert-butyl ether, trichloromethane, butanone, butyl acetate, valerolactone and butyrolactone.

As a further embodiment of the present application: the volume ratio of the organic solvent to the sugar-containing raw material is in a range of 0.5:1-10:1.

As a further embodiment of the present application: during the reaction in Step S2, nitrogen is charged to make the reaction pressure 0.1-6 MPa, the reaction flow rate is 1-100 mL/min, the reaction time is 0.1-10 min, and the reaction temperature is 50-200° C.

As a further embodiment of the present application: the tin loading of the humin-supported Sn catalyst is 0.5%-9%.

As a further embodiment of the present application: the humin-supported Sn catalyst is fixed in a tubular reactor R01, in which the filling volume of the catalyst bed accounts for 50%-100% of the reactor, and the balance is filler.

As a further embodiment of the present application: the reaction device comprises a balance, a metering pump P01 and a metering pump P02, a tubular reactor R01, a condenser E01, an oil bath circulation tank F01, a gas-liquid separation tank V01, a sampling valve group, and a collection tank.

As a further embodiment of the present application: the sugar-containing raw material and the organic solvent are placed in two feed bottles respectively, and after preheating, they are transported to the tubular reactor R01 by the metering pump P01 and metering pump P02 for heated reaction. After the reaction, the obtained product is cooled by the condenser E01 and separated by the gas-liquid separation tank V01, and then the reaction liquid is collected in the collection tank V02, and the product 5-HMF is separated and purified after being discharged by the discharge valve.

As a further embodiment of the present application: the tubular reactor R01 is heated by the oil bath circulation tank F01, and a water chiller F02 provides a constant flow of cooling water for the condenser E01.

As a further embodiment of the present application: after the reaction system reacts in the tubular reactor R01, the water vapor and product vapor are taken out by nitrogen, and the gas phase and liquid phase are separated in the gas-liquid separation tank through the condenser, and the gas generated by the reaction can be safely emptied through the valve.

As a further embodiment of the present application: the sampling valve group is connected to the gas-liquid separation tank V01, and the sampling valve group can realize inline sampling of the reaction liquid, so as to timely monitor the preparation of 5-HMF.

Beneficial effects of the present application:

The present application synthesizes a humin-supported Sn catalyst and applies it to catalyze biomass sugars (such as fructose syrup, glucose syrup, high fructose corn syrup, waste molasses, and straw syrup) to prepare 5-HMF. The biomass syrup used in the present application is easy to obtain. For example, the high fructose corn syrup containing a large amount of fructose is obtained by hydrolyzing corn starch and is an ideal raw material for preparing 5-HMF. In addition, the present application rationally utilizes industrial waste humin to prepare a catalyst, which has an important role in promoting the hydrolysis of sugars to prepare high value-added chemicals. Considering that tin-based catalysts have good activity in sugar dehydration reactions, the introduction of tin into humin-based catalysts is beneficial to the isomerization and dehydration reactions of sugars. The catalyst has the advantages of simple preparation, mild reaction conditions, and low cost, and has a good catalytic effect on the synthesis of 5-HMF from sugars.

In the present application, biomass sugar is used as a raw material, and self-made humin-support Sn is used as a catalyst. After a certain reaction time, a reaction liquid containing 5-HMF is obtained, and 5-HMF is obtained after separation and purification. The present application rationally utilizes industrial waste humin to prepare a humin-supported Sn catalyst, which has an important role in promoting the hydrolysis of sugars to prepare high value-added chemicals, and the catalyst has the advantages of a simple preparation method and mild reaction conditions.

The present application can incorporate an inline monitoring equipment to monitor the production of 5-HMF in real time. The tubular reactor used can reduce backmixing, greatly shorten the reaction time and reduce the generation of by-products such as humin, providing ideas for realizing industrial-scale production. In summary, the present application has the advantages of simple process, mild reaction conditions, low energy consumption, high yield, cost saving, etc.

BRIEF DESCRIPTION OF THE DRAWINGS

The present application is further described below in conjunction with the accompanying drawings.

DETAILED DESCRIPTION

The following will be combined with examples of the present application to clearly and completely describe the technical solutions in the embodiments of the present application. Obviously, the described examples are only part of the examples of the present application, not all of them. Based on the examples of the present application, all other examples obtained by ordinary technicians in the field without creative efforts are within the scope of protection of the present application.

Example 1

A method for synthesizing 5-HMF comprises the following steps:

S1. Preparation of humin-supported Sn catalyst: drying and then grinding the separated humin at high temperature into dry powder, and suspending the dry powder in water to obtain a humin suspension; meanwhile dissolving $SnCl_4 \cdot 5H_2O$ in water to prepare a 10% $SnCl_4 \cdot 5H_2O$ solution, adding the humin suspension to the 10% $SnCl_4 \cdot 5H_2O$ solution under rapid stirring, stirring continuously for 2 hours after addition, standing overnight for aging, performing concentration to dryness, performing vacuum drying to remove water, grinding the resultant into powder, and calcining the powder under nitrogen. The calcination procedure was as follows: under a nitrogen atmosphere, heating to 200° C. within 1 hour, maintaining for 6 hours, then heating to 550° C. within 2 hours, maintaining for 6 hours. After cooling to room temperature, a humin-supported Sn catalyst was obtained.

S2. Preparation of 5-hydroxymethylfurfural: placing a sugar raw material aqueous solution and an organic solvent in two feed bottles respectively, fixing the humin-supported Sn catalyst in a tubular reactor, and filling the catalyst bed to 100 mL. The reaction was carried out in the tubular reactor under a nitrogen atmosphere, with a reaction pressure of 0.1-6 MPa, a reaction flow rate of 1-100 mL/min, and a reaction time of 0.1-10 min at 50-200° C. A reaction liquid containing 5-HMF was obtained by the continuous reaction, and pure 5-HMF was obtained after purification.

Figure 1:
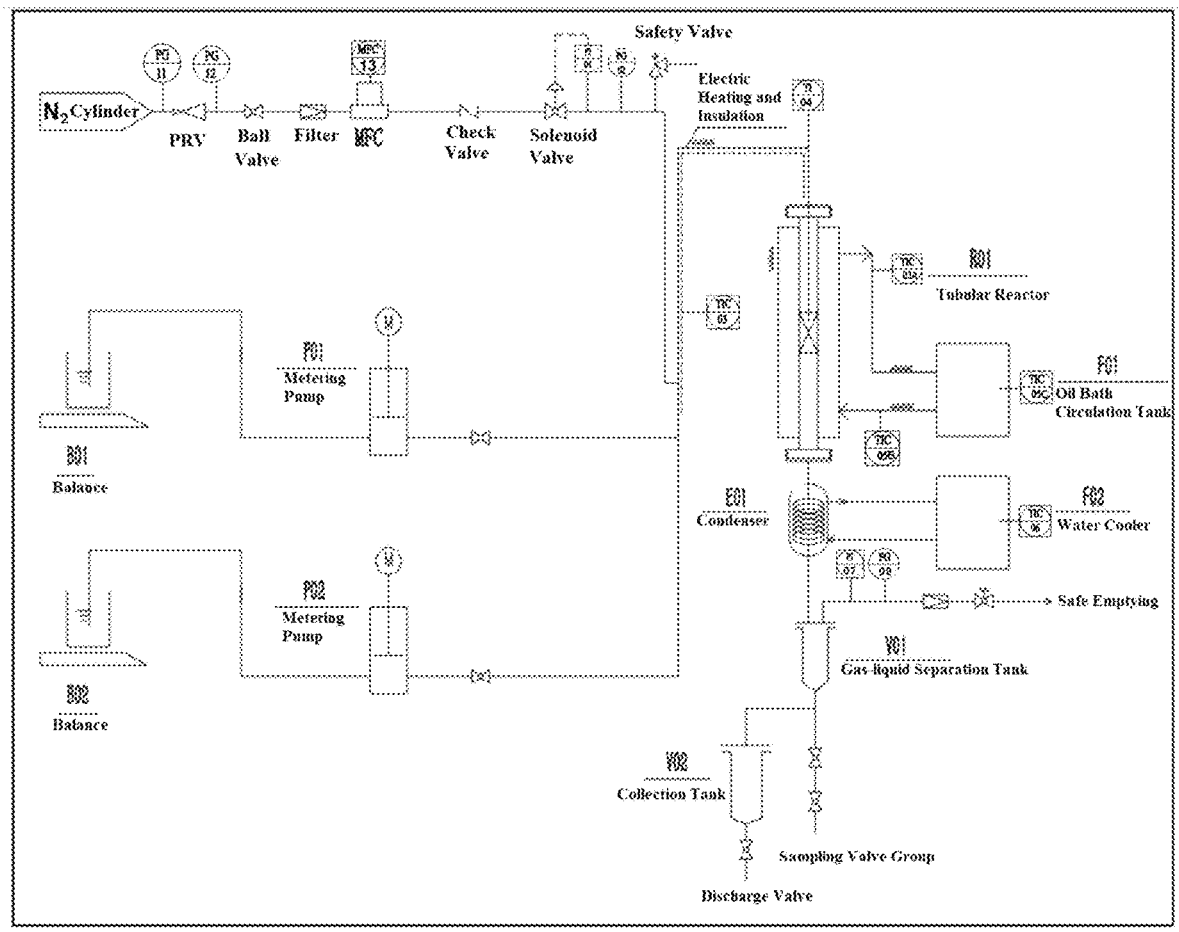
FIG. 1 is a flow chart of the reaction device in the present application.

The device for synthesizing 5-HMF in this example is shown in FIG. 1. The reaction device comprises components such as a balance, a metering pump P01 and a metering pump P02, a tubular reactor R01, a condenser E01, an oil bath circulation tank F01, a gas-liquid separation tank V01, a sampling valve group, and a collection tank. The tubular reactor R01 was heated by the oil bath circulation tank F01, and a water chiller F02 provided a constant flow of cooling water for the condenser E01.

During working, the sugar-containing raw material aqueous solution and the solvent were placed in two feed bottles respectively, and after preheating, they were transported to the tubular reactor R01 by the metering pump P01 and the metering pump P02 for heated reaction. After the reaction, the obtained product was cooled by the condenser E01 and separated by the gas-liquid separation tank V01, and then the reaction liquid was collected in the collection tank V02. The product 5-HMF was separated and purified after being discharged by the discharge valve.

Meanwhile, the flow rate of the sugar raw material aqueous solution and the solvent was controlled by adjusting the metering pump P01 and metering pump P02; after the reaction system reacts in the tubular reactor, the water vapor and product vapor were taken out by nitrogen, and the gas phase and liquid phase were separated in the gas-liquid separation tank through the condenser, and the gas generated by the reaction could be safely emptied through the valve; in addition, the sampling valve group was connected to the gas-liquid separation tank V01, and the sampling valve group could realize inline sampling of the reaction liquid, so as to monitor the preparation status of 5-HMF in time.

Example 2

A method for synthesizing 5-HMF comprises the following steps:

S1. Preparation of humin-supported Sn catalyst: drying and then grinding the separated humin at high temperature into 52.5 g dry powder, and suspending the dry powder in 525 g water to obtain a humin suspension; meanwhile dissolving 7.7 g $SnCl_4 \cdot 5H_2O$ in 69.3 g water to prepare a 10% $SnCl_4 \cdot 5H_2O$ solution, adding the humin suspension to the 10% $SnCl_4 \cdot 5H_2O$ solution under rapid stirring, stirring continuously for 2 hours after addition, standing overnight for aging, performing concentration to dryness, performing vacuum drying at 120° C. to remove water, grinding the resultant into powder, and calcining the powder under nitrogen. The calcination procedure was as follows: under a nitrogen atmosphere, heating to 200° C. within 1 hour, maintaining for 6 hours, then heating to 550° C. within 2 hours, maintaining for 6 hours. After cooling to room temperature, 28.9 g humin-supported Sn catalyst was obtained, and the tin content was 9%, as detected by ICP.

S2. Preparation of 5-hydroxymethylfurfural: placing 1 L 75% fructose syrup and 9 L acetonitrile in two feed bottles respectively, fixing the humin-supported Sn catalyst in a tubular reactor, and filling the catalyst bed to 100 mL. The reaction was carried out in the tubular reactor under a nitrogen atmosphere, with a reaction pressure of 1 MPa, a reaction flow rate of 20 mL/min (in which the flow rates of fructose syrup and acetonitrile were 2 mL/min and 18 mL/min respectively), and a reaction time of 5 min at 180° C. the sampling valve was opened and samples were take out for detection with detection conditions: Hitachi L2000 HPLC System, Alltech C18 column, mobile phase $CH_3OH$:$H_2O$=20:80, flow rate: 1.0 mL/min, column temperature: 30° C., detector: DAD, and detection wavelength: 284 nm. The product was determined to be 5-hydroxymethylfurfural (5-HMF) by HPLC. A reaction liquid containing 5-HMF was finally obtained by the continuous reaction. After purification, the yield of 5-HMF was measured to be 93% and the purity was 97%.

The device used to synthesize 5-HMF in this example is the same as that in Example 1.

Example 3

A method for synthesizing 5-HMF comprises the following steps:

Compared with Example 2, only the tin loading of the humin-supported Sn catalyst in Step S1 was changed, wherein 2.2 g $SnCl_4 \cdot 5H_2O$ was dissolved in 19.8 g water to prepare a 10% $SnCl_4 \cdot 5H_2O$ solution, and the remaining components and steps were exactly the same. Finally, 25.3 g of the humin-supported Sn catalyst was prepared, and the tin content was 3%, as detected by ICP; the components and steps of Step S2 were exactly the same, and after the reaction, the 5-HMF yield was measured to be 86% and the purity was 98%.

The device used to synthesize 5-HMF in this example is the same as that in Example 1.

Example 4

A method for synthesizing 5-HMF comprises the following steps:

Compared with Example 2, only the tin loading of the humin-supported Sn catalyst in Step S1 was changed, wherein 4.7 g $SnCl_4 \cdot 5H_2O$ was dissolved in 42.3 g water to prepare a 10% $SnCl_4 \cdot 5H_2O$ solution, and the remaining components and steps were exactly the same. Finally, 26.3 g of the humin-supported Sn catalyst was prepared, and the tin content was 6%, as detected by ICP; the components and steps of Step S2 were exactly the same, and after the reaction, the 5-HMF yield was measured to be 90% and the purity was 98%.

The device used to synthesize 5-HMF in this example is the same as that in Example 1.

Example 5

A method for synthesizing 5-HMF comprises the following steps:

Compared with Example 2, only the reaction temperature of Step S2 was changed to 160° C., and the other components and steps were exactly the same. After the reaction, the yield of 5-HMF was measured to be 80% and the purity was 98%.

The device used to synthesize 5-HMF in this example is the same as that in Example 1.

Example 6

A method for synthesizing 5-HMF comprises the following steps:

Compared with Example 2, only the reaction temperature of Step S2 was changed to 170° C., and the other components and steps were exactly the same. After the reaction, the yield of 5-HMF was measured to be 84% and the purity was 97%.

The device used to synthesize 5-HMF in this example is the same as that in Example 1.

Example 7

A method for synthesizing 5-HMF comprises the following steps:

Compared with Example 2, only the reaction temperature of Step S2 was changed to 200° C., and the other components and steps were exactly the same. After the reaction, the yield of 5-HMF was measured to be 82% and the purity was 97%.

The device used to synthesize 5-HMF in this example is the same as that in Example 1.

Example 8

A method for synthesizing 5-HMF comprises the following steps:

Compared with Example 2, only the reaction flow rate of Step S2 was changed to 33 mL/min (the flow rates of fructose syrup and acetonitrile were 3.3 mL/min and 29.7 mL/min respectively), and the other components and steps were exactly the same. After the reaction, the yield of 5-HMF was measured to be 80% and the purity was 98%.

The device used to synthesize 5-HMF in this example is the same as that in Example 1.

Example 9

A method for synthesizing 5-HMF comprises the following steps:

Compared with Example 2, only the reaction flow rate of Step S2 was changed to 14 mL/min (the flow rates of fructose syrup and acetonitrile were 1.4 mL/min and 12.6 mL/min respectively), and the other components and steps were exactly the same. After the reaction, the yield of 5-HMF was measured to be 85% and the purity was 98%.

The device used to synthesize 5-HMF in this example is the same as that in Example 1.

Example 10

A method for synthesizing 5-HMF comprises the following steps:

Compared with Example 2, only the reaction flow rate of Step S2 was changed to 10 mL/min (the flow rates of fructose syrup and acetonitrile were 1 mL/min and 9 mL/min respectively), and the other components and steps were exactly the same. After the reaction, the yield of 5-HMF was measured to be 83% and the purity was 97%.

The device used to synthesize 5-HMF in this example is the same as that in Example 1.

Example 11

A method for synthesizing 5-HMF comprises the following steps:

Compared with Example 2, only the reaction pressure of Step S2 was changed to 0.5 MPa, and the other components and steps were exactly the same. After the reaction, the yield of 5-HMF was measured to be 91% and the purity was 98%.

The device used to synthesize 5-HMF in this example is the same as that in Example 1.

Example 12

A method for synthesizing 5-HMF comprises the following steps:

Compared with Example 2, only the reaction pressure of Step S2 was changed to 2 MPa, and the other components and steps were exactly the same. After the reaction, the yield of 5-HMF was measured to be 94% and the purity was 98%.

The device used to synthesize 5-HMF in this example is the same as that in Example 1.

Example 13

A method for synthesizing 5-HMF comprises the following steps:

Compared with Example 2, only the reaction solvent of Step S2 was changed to acetone, and the other components and steps were exactly the same. After the reaction, the yield of 5-HMF was measured to be 83% and the purity was 98%.

The device used to synthesize 5-HMF in this example is the same as that in Example 1.

Example 14

A method for synthesizing 5-HMF comprises the following steps:

Compared with Example 2, only the reaction solvent of Step S2 was changed to tetrahydrofuran, and the other components and steps were exactly the same. After the reaction, the yield of 5-HMF was measured to be 88% and the purity was 98%.

The device used to synthesize 5-HMF in this example is the same as that in Example 1.

Example 15

A method for synthesizing 5-HMF comprises the following steps:

Compared with Example 2, only the reaction solvent of Step S2 was changed to ethyl acetate, and the other components and steps were exactly the same. After the reaction, the yield of 5-HMF was measured to be 80% and the purity was 97%.

The device used to synthesize 5-HMF in this example is the same as that in Example 1.

Example 16

A method for synthesizing 5-HMF comprises the following steps:

Compared with Example 2, the 1 L 75% fructose syrup and 9 L acetonitrile of Step S2 were changed to 3 L 75% fructose syrup and 7 L acetonitrile, and the flow rates of fructose syrup and acetonitrile were changed to 6 mL/min and 14 mL/min respectively, and the other components and steps were exactly the same. After the reaction, the yield of 5-HMF was measured to be 86% and the purity was 98%.

The device used to synthesize 5-HMF in this example is the same as that in Example 1.

Example 17

A method for synthesizing 5-HMF comprises the following steps:

Compared with Example 2, the 1 L 75% fructose syrup and 9 L acetonitrile of Step S2 were changed to 5 L 75% fructose syrup and 5 L acetonitrile, and the flow rates of fructose syrup and acetonitrile were changed to 10 mL/min and 10 mL/min respectively, and the other components and steps were exactly the same. After the reaction, the yield of 5-HMF was measured to be 81% and the purity was 98%.

The device used to synthesize 5-HMF in this example is the same as that in Example 1.

Example 18

A method for synthesizing 5-HMF comprises the following steps:

Compared with Example 2, only the 75% fructose syrup of Step S2 was changed to 50% fructose syrup, and the other components and steps were exactly the same. After the reaction, the yield of 5-HMF was measured to be 88% and the purity was 97%.

The device used to synthesize 5-HMF in this example is the same as that in Example 1.

Example 19

A method for synthesizing 5-HMF comprises the following steps:

Compared with Example 2, only the 75% fructose syrup of Step S2 was changed to 25% fructose syrup, and the other components and steps were exactly the same. After the reaction, the yield of 5-HMF was measured to be 83% and the purity was 98%.

The device used to synthesize 5-HMF in this example is the same as that in Example 1.

Example 20

A method for synthesizing 5-HMF comprises the following steps:

Compared with Example 2, only the 75% fructose syrup of Step S2 was changed to 75% glucose syrup, and the other components and steps were exactly the same. After the reaction, the yield of 5-HMF was measured to be 80% and the purity was 97%.

The device used to synthesize 5-HMF in this example is the same as that in Example 1.

Example 21

A method for synthesizing 5-HMF comprises the following steps:

Compared with Example 2, only the 75% fructose syrup of Step S2 was changed to 75% high fructose corn syrup, and the other components and steps were exactly the same. After the reaction, the yield of 5-HMF was measured to be 90% and the purity was 96%.

The device used to synthesize 5-HMF in this example is the same as that in Example 1.

Example 22

A method for synthesizing 5-HMF comprises the following steps:

Compared with Example 2, only the 75% fructose syrup of Step S2 was changed to 50% straw syrup, and the other components and steps were exactly the same. After the reaction, the yield of 5-HMF was measured to be 70% and the purity was 98%.

The device used to synthesize 5-HMF in this example is the same as that in Example 1.

Example 23

A method for synthesizing 5-HMF comprises the following steps:

Compared with Example 2, only the 75% fructose syrup of Step S2 was changed to 50% waste molasses, and the other components and steps were exactly the same. After the reaction, the yield of 5-HMF was measured to be 70% and the purity was 98%.

The device used to synthesize 5-HMF in this example is the same as that in Example 1.

Figure 2:
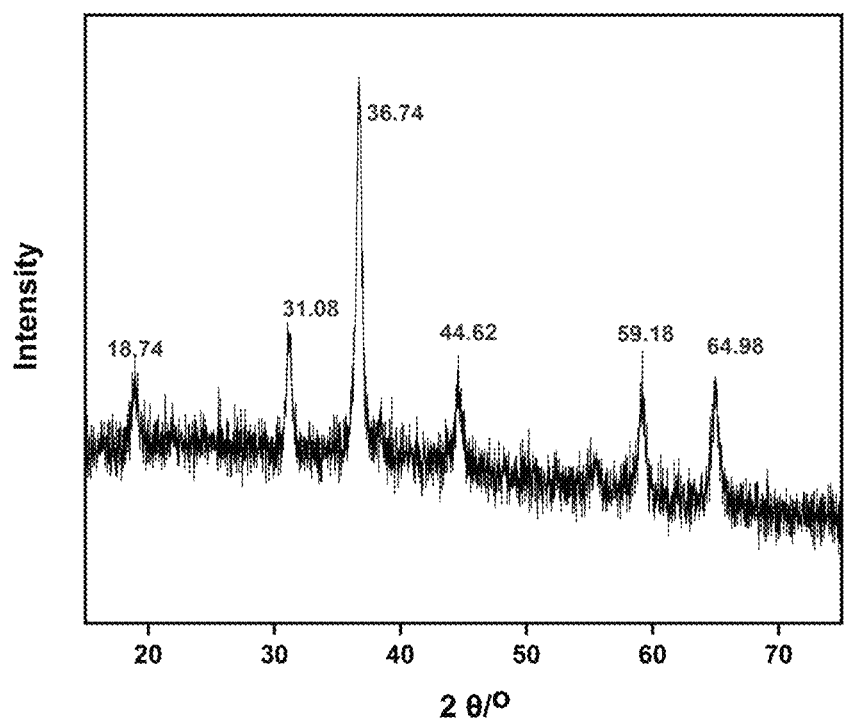
FIG. 2 is an XRD spectrum of the humin-supported Sn catalyst in the present application.
Figure 3:
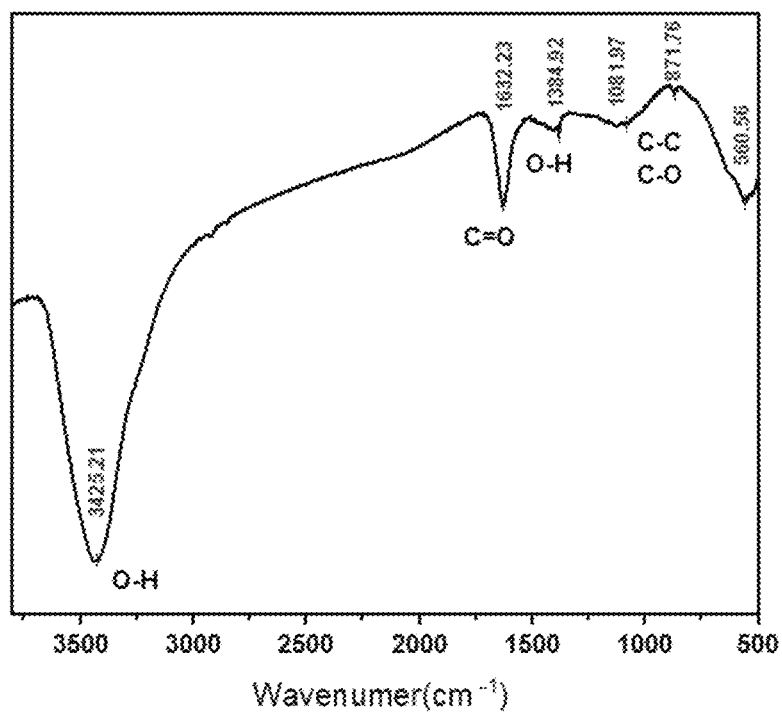
FIG. 3 is a Fourier Transform Infrared Spectroscopy (FTIR) analysis diagram of the humin-supported Sn catalyst in the present application.
Figure 4:
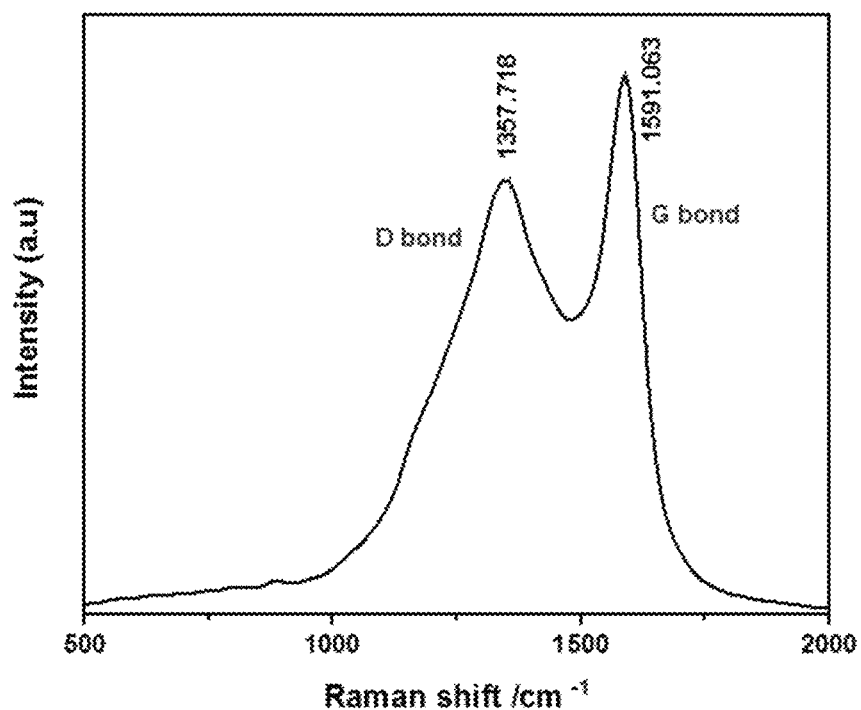
FIG. 4 is a Raman spectrum diagram of the humin-supported Sn catalyst in the present application.
Figure 5:
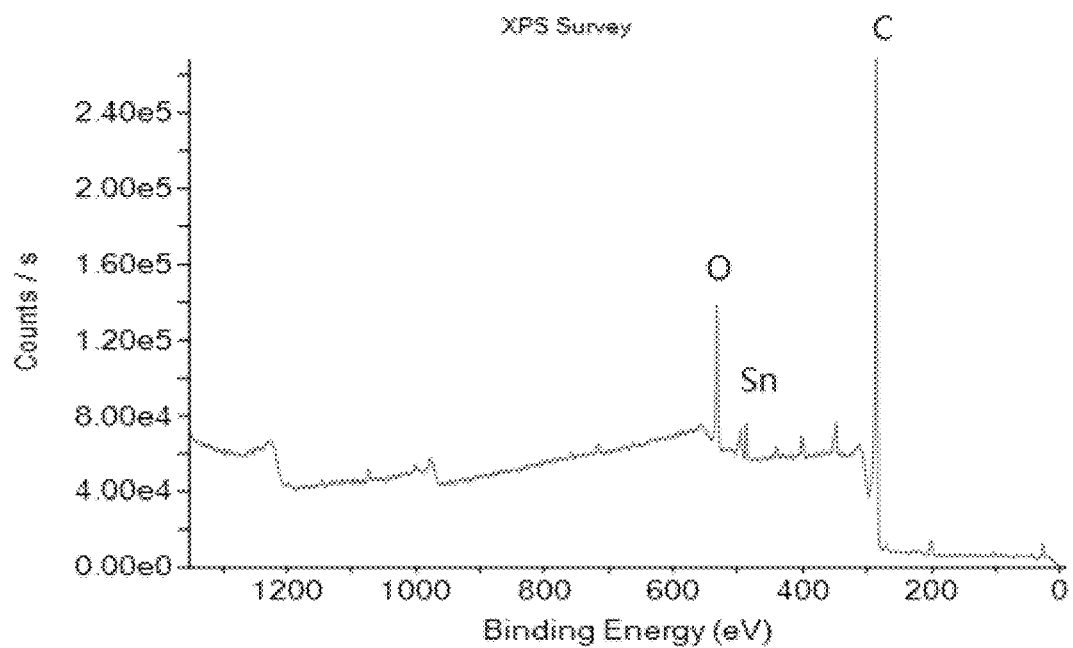
FIG. 5 is an XPS diagram of the humin-supported Sn catalyst in the present application.

In Example 2, the prepared humin-supported Sn catalyst was characterized, and the tin content was detected by ICP to be 9%; the BET results showed that the specific surface area of the catalyst was 158.3027 m$^2$/g, and the larger specific surface area was conducive to the contact between the active neutral Sn species and the substrate, thereby facilitating the activation of the substrate and the reaction; the XRD spectrum of the humin-supported Sn catalyst is shown in FIG. 2, from which it can be seen that the catalyst contains obvious diffraction peaks of the SnO$_2$ phase; the Fourier Transform Infrared Spectroscopy (FTIR) analysis diagram of the humin-supported Sn catalyst is shown in FIG. 3, which indicates the types of surface functional groups on the carbon carrier, i.e., carboxyl groups (C—O stretching vibration at 1081 cm$^{-1}$, and C=O stretching vibration at 1632 cm$^{-1}$), alcohol functional groups (—OH in-plane bending at 1384 cm$^{-1}$, and —OH stretching vibration at 3425 cm$^{-1}$) and furan rings (C—O stretching vibration at 871 cm$^{-1}$); the Raman spectrum of the humin-supported Sn catalyst is shown in FIG. 4, from which the structural information of the carbon material can be obtained, the figure shows that there are two characteristic peaks located at the D band (1346 cm$^{-1}$) and the G band (1588 cm$^{-1}$). The D band (sp$^3$ carbon) is related to graphene defects caused by pentagons or heptagons and indicates the surface defects and disorder of the carbon carrier, while the G band corresponds to the in-plane stretching vibration of sp$^2$ carbon atoms, indicating that the carbon carrier has a graphene structure in the order of C atoms; and the XPS graph of the humin-supported Sn catalyst is shown in FIG. 5, from which it can be seen that the catalyst contains Sn, O, and C elements. The above analysis shows that the catalyst prepared using humin as a carrier has obvious active Sn substances, and the carrier has a large specific surface area, which is conducive to the combination of active centers and substrates. In addition, the existing graphene structure is conducive to the transfer of electrons and the regeneration of centers, which together give the catalyst high catalytic activity.

Through Examples 2-4 and 8-10, it can be seen that the reaction flow rate (retention time) and the tin loading of the catalyst under the same other conditions have a comprehensive impact on the yield of the product. The greater the reaction flow rate, the shorter the retention time, and the higher the catalyst loading, the higher the reaction yield. When the reaction time is 5 minutes and the tin loading is 9%, the 5-HMF yield is 93%, which is the best. Under the same other conditions, when the reaction retention time exceeds 5 minutes, the product yield begins to decrease, which is mainly attributed to the decomposition and polymerization of the product, therefore, the optimal reaction time is 5 minutes. Through Examples 2 and 5-7, it can be seen that under the same other conditions, the 5-HMF yield increases with the increase of reaction temperature below 180° C., but above 180° C., the yield decreases slightly with the increase of temperature, mainly because the rate of by-product generation is also increasing and the product further undergoes other reactions. Through Examples 2 and 11-12, it can be seen that the nitrogen pressure has little effect on the reaction yield. Through Examples 2 and 13-15, it can be seen that when reacting in different solvents (acetone, acetonitrile, tetrahydrofuran, and ethyl acetate), the reaction yield is the highest when acetonitrile is used as the solvent under the same other conditions, followed by tetrahydrofuran. Through Examples 2 and 16-19, it can be seen that changing the ratio of solvent to fructose syrup and the mass fraction of fructose syrup can improve the yield of the product. Through Examples 2 and 20-23, it can be seen that among the different types of sugars (fructose syrup, glucose syrup, high fructose corn syrup, straw syrup, and waste molasses) as reaction raw material, the reaction yield of fructose syrup is the highest, followed by high fructose corn syrup.

Through the above examples, it can be found that the reaction flow rate, temperature, pressure, sugar type and concentration, organic solvent, catalyst tin loading, etc. are all factors that affect the yield of 5-HMF. By screening and optimizing experimental conditions and controlling experimental variables, the conversion rate of the reaction can be improved, which also provides new ideas and directions for us to obtain a higher yield of 5-HMF next.

In summary, the present application provides a method for preparing 5-HMF, which uses biomass sugar as raw material and self-made tin on humin as a catalyst. After a certain reaction time, a reaction liquid containing 5-HMF is obtained, and 5-HMF is obtained after separation and purification. The present application rationally utilizes industrial waste humin to prepare a humin-supported Sn catalyst that has high catalytic activity and has the advantages of a simple preparation method and mild reaction conditions, which has an important role in promoting the hydrolysis of sugars to prepare high value-added chemicals. In addition, the present application incorporates inline monitoring equipment to monitor the production of 5-HMF in real time. The tubular reactor used can reduce backmixing, greatly shorten the reaction time and reduce the generation of humin, providing ideas for realizing industrial-scale production. Therefore, the present application has the advantages of simple process, mild reaction conditions, low energy consumption, high yield, cost saving, etc.

It should be noted that relational terms herein such as first and second are only used to distinguish one entity or operation from another entity or operation, and do not necessarily require or imply any such actual relationship or order between these entities or operations. Moreover, the terms "include", "comprises/comprising", or any other variation thereof are intended to cover non-exclusive inclusion, so that a process, method, article or device including a series of elements includes not only those elements, but also includes other elements not explicitly listed, or also includes elements inherent to such process, method, article or device.

Although the embodiments of the present application have been shown and described, it is understood by those skilled in the art that various changes, modifications, substitutions and variations may be made to these embodiments without departing from the principles and spirit of the present application, and the scope of the present application is defined by the appended claims and their equivalents.

What is claimed is:

1. A method for preparing 5-hydroxymethylfurfural, comprising the following steps:
   step S1, drying and then grinding humin into a first powder, suspending the first powder in water to obtain a suspension, adding a tin tetrachloride aqueous solution under rapid stirring to the suspension, stirring continuously after the addition, standing overnight for aging, performing concentrating and drying, grinding the resultant into a second powder, and calcining the second powder in air to obtain a tin on humin catalyst;
   step S2, injecting a sugar-containing raw material and an organic solvent using a metering pump into a reaction device filled with the tin on humin catalyst for reaction respectively, and after the reaction, performing separation and purification to obtain 5-hydroxymethylfurfural;
   wherein the sugar-containing raw material is at least one of fructose syrup, glucose syrup, high fructose corn syrup, waste molasses and straw syrup.

2. The method of claim 1, wherein the concentration of the fructose syrup, glucose syrup and high fructose corn syrup is 1%-75%, and the concentration of the waste molasses and straw syrup is 1%-50%.

3. The method of claim 1, wherein the organic solvent is at least one of ethyl acetate, acetonitrile, tetrahydrofuran, acetone, toluene, methyl isobutyl ketone, dimethyl sulfoxide, N,N-dimethylformamide, N,N-dimethylacetamide, N-methylpyrrolidone, 2-methyltetrahydrofuran, dimethyl carbonate, 1,4-dioxane, methanol, isopropanol, n-butanol, methyl tert-butyl ether, trichloromethane, butanone, butyl acetate, valerolactone and butyrolactone.

4. The method of claim 1, wherein the volume ratio of the organic solvent to the sugar-containing raw material is in a range of 0.5:1-10:1.

5. The method of claim 1, wherein during the reaction in Step S2, nitrogen is charged to make the reaction pressure 0.1-6 MPa, the reaction flow rate is 1-100 mL/min, the reaction time is 0.1-10 min, and the reaction temperature is 50-200° C.

6. The method of claim 1, wherein the tin loading of the tin on humin catalyst is 0.5%-9%.

7. The method of claim 1, wherein the tin on humin catalyst is fixed in a tubular reactor, in which the filling volume of the catalyst bed accounts for 50%-100% of the reactor, and the balance is filler.

8. The method of claim 1, wherein the reaction device comprises a balance, a liquid inlet metering pump, a tubular reactor, a condenser, an oil bath circulation tank, a gas-liquid separation tank, a sampling valve group, and a collection tank, wherein two liquid inlet metering pumps are used to input the sugar-containing raw material aqueous solution and the solvent into the tubular reactor for mixing and reacting.

* * * * *